US012763199B2

(12) United States Patent
Stefanov

(10) Patent No.: US 12,763,199 B2
(45) Date of Patent: Oct. 13, 2026

(54) HUB DEVICE FOR A PORTABLE MEDICAL DEVICE

(71) Applicant: SHL MEDICAL AG, Zug (CH)

(72) Inventor: Slobodan Stefanov, Deerfield Beach, FL (US)

(73) Assignee: SHL Medical AG, Zug (CH)

( * ) Notice: Subject to any disclaimer, the term of this patent is extended or adjusted under 35 U.S.C. 154(b) by 1052 days.

(21) Appl. No.: 17/915,080

(22) PCT Filed: Apr. 21, 2021

(86) PCT No.: PCT/EP2021/060387
§ 371 (c)(1),
(2) Date: Sep. 27, 2022

(87) PCT Pub. No.: WO2021/219460
PCT Pub. Date: Nov. 4, 2021

(65) Prior Publication Data

US 2023/0154604 A1 May 18, 2023

Related U.S. Application Data

(60) Provisional application No. 63/016,996, filed on Apr. 29, 2020.

(30) Foreign Application Priority Data

May 22, 2020 (EP) .................................... 20176053

(51) Int. Cl.
*G16H 40/63* (2018.01)
*A61M 5/172* (2006.01)
(Continued)

(52) U.S. Cl.
CPC ............ *G16H 40/63* (2018.01); *A61M 5/172* (2013.01); *A61M 15/0001* (2014.02);
(Continued)

(58) Field of Classification Search
CPC ........ G16H 40/63; G16H 20/13; G16H 20/17; A61M 5/172; A61M 15/0001;
(Continued)

(56) References Cited

U.S. PATENT DOCUMENTS 5,334,173 A 8/1994 Armstrong, Jr.
8,920,376 B2 12/2014 Caffey et al.
(Continued)

FOREIGN PATENT DOCUMENTS

WO 2012/109277 A1 8/2012
WO WO-2019099568 A1 * 5/2019 ............ A61M 5/142
WO 2019/121613 A1 6/2019

OTHER PUBLICATIONS

International Search Report and Written Opinion for Int. App. No. PCT/EP2021/062849, mailed May 28, 2021.

*Primary Examiner* — Valerie L Woodward
(74) *Attorney, Agent, or Firm* — McDonnell Boehnen & Berghoff LLP

(57) ABSTRACT

A hub device configured to enable wireless communication between portable medical devices and an external device, where the hub device has a radio transceiver device configured to receive portable medical device data from each portable medical device and configured to transmit received portable medical device data to the external device, an energy storage unit configured to power the radio transceiver device, and an energy harvesting circuit configured to harvest radio frequency energy to charge the energy storage unit, wherein the hub device is configured to communicate with the portable medical devices using a protocol that for each portable medical device enables a unique portable medical device identifier to be included in the portable medical device data, and wherein the hub device has processing circuitry configured to establish a communications link with a portable medical device if the processing cir-
(Continued)

cuitry confirms recognition of the unique portable medical device identifier received from the portable medical device.

18 Claims, 1 Drawing Sheet

(51) Int. Cl.
*A61M 5/20* (2006.01)
*A61M 15/00* (2006.01)
*H04L 67/12* (2022.01)

(52) U.S. Cl.
CPC ............... *A61M 2005/2006* (2013.01); *A61M 2205/3561* (2013.01); *A61M 2205/3584* (2013.01); *H04L 67/12* (2013.01)

(58) Field of Classification Search
CPC .. A61M 2005/2006; A61M 2205/3561; A61M 2205/3584; A61M 2205/3592; A61M 2205/3546; A61M 2205/3553; A61M 2205/3569; A61M 2205/3576; A61M 2205/50; A61M 2205/502; H04L 67/12; H04L 67/125
See application file for complete search history.

(56) References Cited

U.S. PATENT DOCUMENTS

| | | | |
|---|---|---|---|
| 10,137,246 | B2 | 11/2018 | Estes et al. |
| 10,383,996 | B2 | 8/2019 | Miller et al. |
| 2009/0058635 | A1 | 3/2009 | LaLonde et al. |
| 2014/0113553 | A1 | 4/2014 | Brukalo et al. |
| 2015/0290396 | A1 | 10/2015 | Nagar et al. |
| 2017/0098058 | A1 | 4/2017 | McCullough et al. |
| 2017/0274149 | A1 * | 9/2017 | Aeschlimann ........... H04Q 9/00 |
| 2017/0347940 | A1 * | 12/2017 | Carr ....................... A61B 5/145 |
| 2018/0182491 | A1 | 6/2018 | Belliveau et al. |
| 2019/0206569 | A1 * | 7/2019 | Shelton, IV ....... A61B 18/1206 |

* cited by examiner

HUB DEVICE FOR A PORTABLE MEDICAL DEVICE

CROSS REFERENCE TO RELATED APPLICATIONS

The present application is a U.S. National Phase Application pursuant to 35 U.S.C. § 371 of International Application No. PCT/EP2021/060387 filed Apr. 21, 2021, which claims priority to U.S. Provisional Application No. 63/016,996, filed Apr. 29, 2020 and European Patent Application No. 20176053.5 filed May 22, 2020. The entire disclosure contents of these applications are herewith incorporated by reference into the present application.

TECHNICAL FIELD

The present disclosure generally relates to portable medical devices such as medicament delivery devices and add-on devices configured to communicate wirelessly.

BACKGROUND

Portable medical devices such as auto-injectors, pen injectors, and inhalers may be configured to communicate with external devices such as smartphones or tablet computers. Such portable medical devices may be configured to transmit portable medical device data which for example may include the date and time that a dose was delivered and/or the given dose size, and/or a unique identifier of the portable medical device in question. The portable medical device data may be used to ensure compliance with for instance a dosage regimen specified by a physician for a specific user.

WO2019/121613 discloses an injection device such as an injection pen. The injection device is configured to communicate with an external device such as a smartphone. The injection device is configured to harvest energy from the external device and to transmit injection device data to the external device. The injection device is provided with an electronic module that can be moulded within a component of the injection device or attached to the injection device. The electronics module comprises a sensor, a control component, an energy module and an antenna. The sensor is configured to detect a signal including an indication of medicament amount associated with a function of the injection device such as a displacement of a plunger rod. This signal can include an electric signal, an acoustic signal, a mechanical signal, and/or an optical signal. The sensor can be configured to generate an electric signal that is proportional to the amount of medicament stored in a medicament reservoir or dispensed by the injection device. Further, the sensor can include an incremental dosing sensor configured to measure an amount of expelled medicament. The control component is an ultra-low power platform chip. The control component is configured to retrieve energy from the energy module and to process the signal received from the sensor to transmit injection data using the antenna, which may be a radio frequency antenna that can transmit injection device data to the external device.

SUMMARY

Regarding compliance, there are generally two compliance situations for a user: 1) to follow the doctor's orders, and 2) to follow the user guide for the monitoring device/system.

Each injection device of the type disclosed in WO2019/121613 may require a pairing with the external device when first used to set up a communications link because of security settings of external devices such as smartphones and tablet computers. This reduces compliance under point 2) above. For each medical administration occasion users would have to pair the injection device with the external device and users would be less cautions about this than they would be about point 1). This causes a problem of data collection, as a user may forget to pair the injection device with the external device. It follows that it makes it more difficult for the physician to determine whether a deterioration of a condition is the result of not taking the medicament or if another medicament should be used and/or whether another dosage regimen should be used.

There is hence according to a first aspect of the present disclosure provided a radio transceiver device configured to receive portable medical device data from each portable medical device and configured to transmit received portable medical device data to the external device, an energy storage unit configured to power the radio transceiver device, and an energy harvesting circuit configured to harvest radio frequency energy to charge the energy storage unit; wherein the energy storage unit is configured to store the harvested radio frequency energy; wherein the hub device is configured to communicate with the portable medical devices using a protocol that for each portable medical device enables a unique portable medical device identifier to be included in the portable medical device data, and wherein the hub device comprises processing circuitry configured to establish a communications link with a portable medical device if the processing circuitry confirms recognition of the unique portable medical device identifier received from the portable medical device.

The hub device is configured to directly communicate with the portable medical device and transmit received portable medical device data to the external device, thereby no manual pre-pairing is required between the external device and the portable medical device.

The portable medical devices are directly able to communicate with the hub device without any manual set up required in case the unique portable medical device identifier is recognised. The risk that a user forgets to pair the portable medical device with the hub device is thus eliminated and compliance under point 2) can therefore better be followed.

According to one embodiment the processing circuitry is configured to enable wireless communication between the hub device and the portable medical device; wherein the processing circuitry is configured to set up a communications link between the hub device and with the portable medical device.

Alternatively, according to another one embodiment the processing circuitry is configured to enable communication between the hub device and the portable medical device by a wire connection; wherein the processing circuitry is configured to set up a communications link between the hub device and with the portable medical device. In this example, both the communication between the hub device and the portable medical devices; and the communication between the portable medical devices and the external device are wireless communication, via the hub device; only the communication between the external device and the hub device is established by wire connection.

According to one embodiment for confirming recognition of the unique portable medical device identifier, the processing circuitry is connected to a storage medium. The storage medium contained a plurality of authorized portable medical device identifiers. When a portable medical device presents within a region that the radio transceiver device of the hub device is able to establish a communication with the portable medical device, the processing circuitry will automatically compare the unique portable medical device identifier received from the portable medical device with the stored authorized portable medical device identifiers in the storage medium. Once the processing circuitry confirms recognition of the unique portable medical device identifier received from the portable medical device, a communication link for exchanging data, especially data except the unique portable medical device identifier, between the hub device and the portable medical device can be established.

Alternatively, according to another embodiment, for confirming recognition of the unique portable medical device identifier, the external device 17 may in turn, using an app, be configured to automatically send the portable medical device identifier received from the portable medical device, within the region that the radio transceiver device of the hub device is able to establish a communication with the portable medical device, to a remote device, e.g. server or cloud. The remote device is configured to perform a comparison between the portable medical device identifier received with a set of portable medical device identifiers. In case of a match, the remote device may send information pertaining to the match to the processing circuitry which thereby can confirm recognition and establish a communications link between the hub device and the portable medical device. In this example, the automatic comparison of the unique portable medical device identifier between a portable medical device and the authorized identifier will be carried out at the remote device side. Therefore, the hub device doesn't need to be equipped with a high storage volume storage medium; and a processing circuitry with high computing power.

According to one embodiment the portable medical devices are medicament delivery devices and/or add-on devices configured to be attached to medicament delivery devices. "Add-on device" may alternatively be referred to as a "supplementary device".

The external device may be a portable or mobile external device. The external device may for example be a smartphone, a tablet computer, a laptop computer, a handheld computer, or a smartwatch.

According to one embodiment the hub device comprises a storage medium comprising a data structure including a plurality of portable medical device identifiers, wherein the processing circuitry is configured to establish the communications link by matching the received unique portable medical device identifier with one of the portable medical device identifiers in the data structure.

If the communications link has not been set up prior to the recognition of the unique portable medical device identifier, the hub device may be configured to send a hub device identifier to the portable medical device so that a communications link may be established.

According to one embodiment the processing circuitry is configured to establish the communications link by matching the unique portable medical device identifier received from the portable medical device with the portable medical device identifier received from the external device.

According to one example, the data structure in the storage medium may be provided with portable medical device identifiers received from the external device. For example, the user's prescription may be sent to the external device and this may include the one or more portable medical device identifiers which is/are received by the hub device.

According to one embodiment the hub device is configured to require an initial manual pairing operation with the external device to enable communication between the hub device and the external device.

The hub device may hence be initially paired manually with an external device to establish a communications link between the hub device and the external device.

According to one embodiment the radio transceiver device is configured to communicate using Bluetooth® and/or Near Field Communication, NFC.

According to one embodiment the radio transceiver device is configured to communicate using local area network-based wireless communication, or cellular network-based wireless communication. The local area network-based communication may for example support any standard in the IEEE 802.11 protocol suite.

According to one embodiment the radio transceiver device is configured to communicate with the portable medical devices using encryption.

According to one embodiment the radio transceiver device is configured to communicate with the external device using encryption.

According to one embodiment the hub device is configured to be mechanically attached to the external device.

According to one embodiment the energy harvesting circuit is configured to harvest radio frequency energy from the external device.

According to one embodiment the hub device is provided with an adhesive layer configured to adhere to the external device and/or the hub device comprises a mechanical attachment member configured to mechanically attach the hub device to the external device.

The present disclosure also provides an operation method of the hub device, the operation method of the hub device.

The mechanical attachment member may for example comprise a snap-fit member or a suction cup.

There is according to a second aspect of the present disclosure provided a system comprising: a hub device as claimed in any of the preceding claims, and a portable medical device configured to wirelessly communicate with the hub device.

According to one embodiment the portable medical device is an injector, an inhaler or an add-on device for a medicament delivery device.

The system may according to one example further comprise the external device.

Generally, all terms used in the claims are to be interpreted according to their ordinary meaning in the technical field, unless explicitly defined otherwise herein. All references to "a/an/the element, apparatus, component, means, etc." are to be interpreted openly as referring to at least one instance of the element, apparatus, component, means, etc., unless explicitly stated otherwise.

BRIEF DESCRIPTION OF THE DRAWINGS

The specific embodiments of the present disclosure will now be described, by way of example, with reference to the accompanying drawings, in which.

DETAILED DESCRIPTION

The present disclosure will now be described more fully hereinafter with reference to the accompanying drawings, in which exemplifying embodiments are shown. The present disclosure may, however, be embodied in many different forms and should not be construed as limited to the embodiments set forth herein; rather, these embodiments are provided by way of example so that this disclosure will be thorough and complete, and will fully convey the scope of the present disclosure to those skilled in the art. Like numbers refer to like elements throughout the description.

Figure 1:
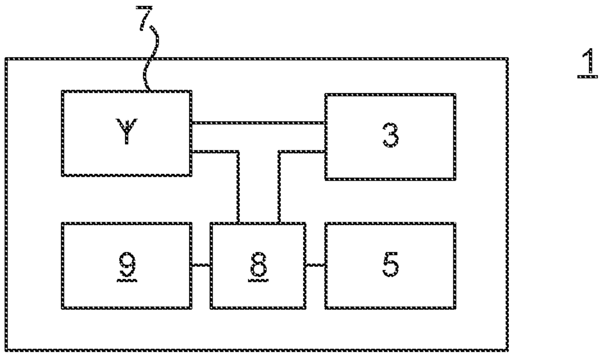
FIG. 1 schematically shows a diagrammatic illustration of an example of a hub device.

FIG. 1 schematically shows an example of a hub device 1. The hub device 1 is a communications device which enables communication between a portable medical device and an external device.

The portable medical device may be a medicament delivery device, or an add-on device configured to be detachably attached to a medicament delivery device. The medicament delivery devices may be single-use or disposable medicament delivery devices. The medicament delivery device may for example be an auto-injector, a pen injector or an inhaler.

The external device may be a portable or mobile external device, such as a smartphone or a tablet computer.

The hub device 1 may be configured to be attached to the external device. The hub device 1 may have a light weight and small size so that it leaves a minimal footprint when attached to the external device.

The hub device 1 may for example be provided with an adhesive layer configured to adhere to the external device. The hub device 1 may have an external surface provided with the adhesive layer. The adhesive of the adhesive layer may be of a type which allows removal of the hub device 1 without damaging the external device.

The hub device 1 may according to one variation comprise a mechanical attachment member configured to mechanically attach the hub device 1 to the external device. The mechanical attachment member may for example be a snap-fit member configured to engage with the external device.

The hub device 1 comprises processing circuitry 3, a radio transceiver device 7, and an energy harvesting circuit 9. The hub device 1 comprises an energy storage unit 8. The energy storage unit 8 may be a battery.

The energy storage unit 8 is configured to power the radio transceiver device 7. The energy storage unit 8 may be configured to power the processing circuitry 3.

The energy harvesting circuit 9 is configured to harvest radio frequency energy to charge or power the energy storage unit 8. The energy harvesting circuit 9 may for example comprise an antenna configured to receive radio frequencies (RF) in a frequency range used by the external device for communication. The energy harvesting circuit 9 may further comprise an impedance matching circuitry, and a rectifier. The energy storage unit 8 is configured to store harvested and rectified RF energy.

The processing circuitry 3 is configured to control the radio transceiver device 7 to establish a communications link between the hub device 1 and portable medical devices. The processing circuitry 3 is configured to enable wireless communication between the hub device 1 and any of a plurality of portable medical devices. The processing circuitry 3 is configured to set up a communications link between the hub device 1 and a portable medical device.

The processing circuitry 3 may for example use any combination of one or more of a suitable central processing unit (CPU), multiprocessor, microcontroller, digital signal processor (DSP), application specific integrated circuit (ASIC), field programmable gate arrays (FPGA) etc., capable of executing any herein disclosed operations confirmation of pre-pairing between the hub device 1 and a portable medical device.

The hub device 1 may comprise a storage medium 5 configured to communicate with the processing circuitry 3. The energy storage unit 8 may be configured to power the storage medium 5.

The storage medium 5 may comprise computer code which when executed by the processing circuitry 3 enables the establishment of a communications link between the hub device 1 and a portable medical device based on the unique portable medical device identifier.

The storage medium 5 may for example be embodied as a memory, such as a random access memory (RAM), a read-only memory (ROM), an erasable programmable read-only memory (EPROM), or an electrically erasable programmable read-only memory (EEPROM) and more particularly as a non-volatile storage medium of a device in an external memory such as a USB (Universal Serial Bus) memory or a Flash memory, such as a compact Flash memory.

The processing circuitry 3 may be configured to provide encrypted communication between the portable medical devices and the external device. The portable medical device data may thus be encrypted.

The processing circuitry 3 may have a very low power consumption, for example in the order of micro Watts.

Figure 2:
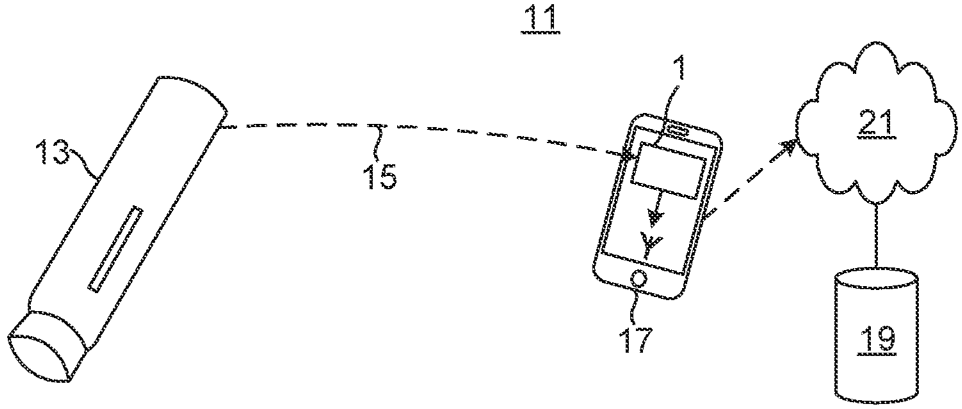
FIG. 2 schematically shows an example of a system including a portable medical device and a hub device.

FIG. 2 shows an example of a system 11. The system 11 comprises a portable medical device 13 and the hub device 1. The portable medical device 13 is a medicament delivery device in this example. The portable medical device 13 comprises circuitry configured to communicate wirelessly with the hub device 1. The portable medical device 13 may also comprise components and circuitry configured to determine for example a dose amount and/or the time and date when medicament is administered by the portable medical device 13. Data of this type will in the following be referred to as administration data. The portable medical device 13 is configured to send portable medical device data to the hub device 1. The portable medical device data may comprise administration data. The protocol used for communication between the portable medical device 13 and the hub device 1 may be configured to enable the portable medical device data to comprise a unique portable medical device identifier. The portable medical device identifier is unique for the portable medical device 13. The portable medical device data may thus contain a unique portable medical device identifier and administration data.

The storage medium 5 may for example comprise a data structure comprising a plurality of portable medical device identifiers.

According to one example of operation of the system 11, the portable medical device 13 may send portable medical device data to the hub device 1, as illustrated by dashed line 15.

The hub device 1 is attached to an external device 17. The energy harvesting circuit 9 harvests RF energy transmitted by the external device 17. The hub device 1 is thus powered by the RF energy harvested from the external device 17.

The processing circuitry 3 is according to one example configured to compare the unique portable medical device identifier contained in the portable medical device data with portable medical device identifiers in the data structure. The processing circuitry 3 is configured to establish a communications link between the portable medical device 13 and the hub device 1 in case a match is found between the unique portable medical device identifier contained in the portable medical device data and one of the portable medical device identifiers of the data structure. In case the communications link is to be established for the first time, the process of pairing may involve the hub device 1 sending a hub device identifier to the portable medical device 13 in case the unique portable medical device identifier is recognised by the hub device 1.

Thus, no manual intervention is required to set up the communications link between the hub device 1 and the portable medical device 13.

The hub device 1 is initially not paired with the external device 17. The hub device 1 is thus typically initially manually paired with the external device 17 to set up a communications link between the hub device 1 and the external device 17. A user may pair the hub device 1 with the external device 17 via a user interface of the external device 17.

When the hub device 1 has been manually paired with the external device 17, the hub device 1 is configured to send portable medical device data sent from the portable medical device 13 to the hub device 1, to the external device 17. Thus, when this pairing has been performed, portable medical device data is sent to the external device 17 via the hub device 1. The external device 17 may be provided with an app configured to handle the portable medical device data received from the hub device 1. The external device 17 may be connected to remote device 19, such as a server, via a cloud network 21 such as the Internet. The external device 17 may be configured to send the portable medical device data to the remote device 19 via the cloud network 21 by means of the app.

When the portable medical device 13 has been used it may be disposed of. The portable medical device 13 may for example be a single use/disposable portable medical device 13. When a user is to use a new portable medical device 13, it will send portable medical device data with a unique portable medical device identifier, which if recognised by the hub device 1, results in the establishment of a communications link between the hub device 1 and the new portable medical device 13. The new portable medical device 13 will thus be able to send portable medical device data to the hub device 1 without manual pairing.

According to another example, the portable medical device 13 may send portable medical device data to the hub device 1. When the hub device 1 and the external device 17 have been paired the hub device 1 may send the portable medical device identifier to the external device 17. The external device 17 may in turn, using the app, be configured to send the portable medical device identifier to the remote device 19, which is configured to perform a comparison between the portable medical device identifier received with a set of portable medical device identifiers. In case of a match, the remote device may send information pertaining to the match to the processing circuitry 3 which thereby can confirm recognition and establish a communications link between the hub device 1 and the portable medical device 13. Alternatively, the remote device 19 may send a list of current portable medical device identifiers to the hub device 1 directly or via the external device 17. Alternatively, one or more portable medical device identifiers may have been manually inputted to the external device, for example, by a doctor, pharmacist or other caregiver through an app. In this case such portable medical device identifier(s) may be sent to the hub device 1 against which the portable medical device identifier received from the portable medical device 13 may be compared for matching by the processing circuitry 3.

It should be noted that the predetermined portable medical device identifiers sent by the external device 17 may be stored in the storage medium 5 first then provided to the processing circuitry 3, or they may directly send to the processing circuitry 3 by the external device 17.

Figure 3:
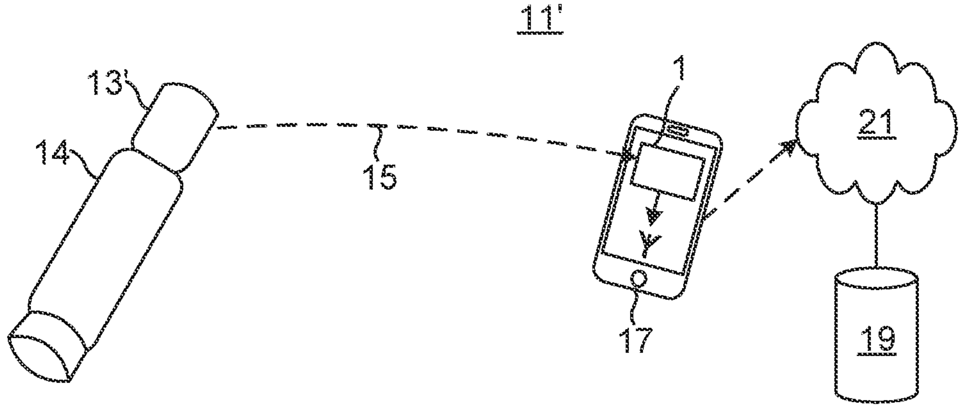
FIG. 3 schematically shows another example of a system including a portable medical device and a hub device.

FIG. 3 depicts another example of system 11. The system 11' is similar to the system shown in FIG. 2. In the example in FIG. 3 the portable medical device 13' is an add-on device configured to be attached to a medicament delivery device 14. The add-on device is thus in this example configured to communicate with the hub device 1. The add-on device is configured to collect administration data from the medicament delivery device 14 and to transmit portable medical device data comprising the administration data. The unique portable medical device identifier is in this case that of the add-on device. The add-on device may be configured to be used with disposable medicament delivery devices.

The present disclosure has mainly been described above with reference to a few examples. However, as is readily appreciated by a person skilled in the art, other embodiments than the ones disclosed above are equally possible within the scope of the present disclosure, as defined by the appended claims.

The invention claimed is:

1. A hub device configured to enable wireless communication between portable medical devices and an external device, wherein the hub device comprises:

a radio transceiver device configured to receive portable medical device data from each portable medical device and configured to transmit received portable medical device data to the external device, an energy storage unit configured to power the radio transceiver device, and an energy harvesting circuit configured to harvest radio frequency energy to charge the energy storage unit; wherein the energy storage unit is configured to store the harvested radio frequency energy;

wherein the hub device is configured to communicate with the portable medical devices using a protocol that for each portable medical device enables a unique portable medical device identifier to be included in the portable medical device data, wherein the hub device comprises processing circuitry configured to establish a communications link with a portable medical device if the processing circuitry confirms recognition of the unique portable medical device identifier received from the portable medical device, wherein the hub device comprises a storage medium comprising a data structure including a plurality of portable medical device identifiers, wherein the processing circuitry is configured to establish the communications link by matching the received unique portable medical device identifier with one of the portable medical device identifiers in the data structure, wherein the unique portable medical device identifiers are configured to be used more than once.

2. The hub device of claim 1, wherein the hub device is configured to directly communicate with the portable medical device and transmit received portable medical device data to the external device, thereby no manual pre-pairing is required between the external device and the portable medical device.

3. The hub device of claim 1, wherein the processing circuitry is configured to enable wireless communication between the hub device and the portable medical device; wherein the processing circuitry is configured to set up the communications link between the hub device and the portable medical device.

4. The hub device of claim 1, wherein the portable medical devices are medicament delivery devices and/or add-on devices configured to be attached to medicament delivery devices.

5. The hub device of claim 1, wherein the processing circuitry is configured to establish the communications link by matching the unique portable medical device identifier received from the portable medical device with a portable medical device identifier received from the external device.

6. The hub device of claim 1, wherein the hub device is configured to require an initial manual pairing operation with the external device to enable communication between the hub device and the external device.

7. The hub device of claim 1, wherein the radio transceiver device is configured to communicate using a short-range radio wave device and/or Near Field Communication, NFC.

8. The hub device of claim 1, wherein the radio transceiver device is configured to communicate using local area network-based wireless communication, or cellular network-based wireless communication.

9. The hub device of claim 1, wherein the radio transceiver device is configured to communicate with the portable medical devices using encryption, wherein the encryption is completed by coding data into an unreadable format and later decoding it to a readable format.

10. The hub device of claim 1, wherein the hub device is configured to be mechanically attached to the external device.

11. The hub device of claim 10, wherein the energy harvesting circuit is configured to harvest radio frequency energy from the external device.

12. The hub device of claim 10, the hub device comprises a mechanical attachment member configured to mechanically attach the hub device to the external device.

13. The hub device of claim 10, wherein the hub device is provided with an adhesive layer configured to adhere to the external device.

14. A system comprising:

a hub device as claimed in claim 1, and a portable medical device configured to wirelessly communicate with the hub device.

15. The system of claim 14, wherein the portable medical device is an injector or an add-on device for a medicament delivery device.

16. The system of claim 14, wherein the portable medical device is an inhaler.

17. A hub device that enables wireless communication between portable medical devices and an external device, where the hub device comprises:

a radio transceiver device that receives portable medical device data from one or more of the portable medical devices, where the radio transceiver device transmits received portable medical device data to the external device;

an energy storage unit that provides power to the radio transceiver device; and an energy harvesting circuit that harvests radio frequency energy to charge the energy storage unit, wherein the energy storage unit stores the harvested radio frequency energy;

wherein the hub device is configured to communicate with the one or more portable medical devices using a protocol that is specific to each portable medical device and enables a unique portable medical device identifier to be included in the portable medical device data, wherein the hub device further comprises processing circuitry configured to establish a communications link with one of the one or more portable medical devices if the processing circuitry confirms recognition of the unique portable medical device identifier received from the portable medical device, wherein the hub device comprises a storage medium comprising a data structure including a plurality of portable medical device identifiers, wherein the processing circuitry is configured to establish the communications link by matching the received unique portable medical device identifier with one of the portable medical device identifiers in the data structure, wherein the unique portable medical device identifiers are configured to be used more than once, and wherein the transmission by the radio transceiver of the received portable medical device data to the external device occurs without manual pre-pairing between the external device and the portable medical device.

18. The hub device of claim 17, wherein the energy harvesting circuit is configured to harvest radio frequency energy from the external device.

* * * * *